(12) United States Patent
Jonsson (10) Patent No.: US 12,178,971 B2
(45) Date of Patent: Dec. 31, 2024

(54) CATHETER DEVICE COMPRISING A LEVERING MEMBER

(71) Applicant: ANESTEASY AB, Uppsala (SE)

(72) Inventor: Ove Jonsson, Uppsala (SE)

(73) Assignee: Anesteasy AB, Uppsala (SE)

( * ) Notice: Subject to any disclaimer, the term of this patent is extended or adjusted under 35 U.S.C. 154(b) by 212 days.

(21) Appl. No.: 17/768,425

(22) PCT Filed: Oct. 9, 2020

(86) PCT No.: PCT/EP2020/078356
§ 371 (c)(1),
(2) Date: Apr. 12, 2022

(87) PCT Pub. No.: WO2021/078535
PCT Pub. Date: Apr. 29, 2021

(65) Prior Publication Data
US 2023/0079239 A1    Mar. 16, 2023

(30) Foreign Application Priority Data
Oct. 23, 2019  (SE) .................................... 1951197-1

(51) Int. Cl.
*A61M 25/01* (2006.01)
*A61M 25/00* (2006.01)
(Continued)

(52) U.S. Cl.
CPC ........ *A61M 25/01* (2013.01); *A61M 25/0097* (2013.01); *A61M 25/0606* (2013.01);
(Continued)

(58) Field of Classification Search
CPC .......... A61M 25/0097; A61M 25/0606; A61M 25/0693; A61M 2025/0006; A61M 2205/582; A61M 2205/583
See application file for complete search history.

(56) References Cited

U.S. PATENT DOCUMENTS 4,292,970 A * 10/1981 Hession, Jr. ...... A61M 25/0606
604/164.01
4,713,057 A * 12/1987 Huttner ............. A61M 25/0612
604/264
(Continued)

FOREIGN PATENT DOCUMENTS

WO    WO 98/57689 A1    12/1998
WO    WO 2017/074682 A1    5/2017
WO    WO 2017/074683 A1    5/2017

OTHER PUBLICATIONS

Office Action dispatched Feb. 6, 2024 for the counterpart Brazilian application No. BR112022006961-8.

*Primary Examiner* — Kami A Bosworth
(74) *Attorney, Agent, or Firm* — Stites & Harbison PLLC; Richard S. Myers, Jr.

(57) ABSTRACT

The disclosure relates to a catheter device (1) comprising a catheter (2), a hypodermic introducer needle (3) and a levering member (23) adapted to be removably attached to the catheter (2) and motion the catheter from a retracted proximal position to an advanced distal position in an axial direction in relation to the introducer needle (3). The catheter device further comprising indicators to indicate the catheter (2) being advanced a distance d corresponding to the length of a beveled tip (18) of the needle (3), and the catheter (2) being advanced a distance D corresponding to a length greater than the length of the beveled tip of the needle (3).

17 Claims, 6 Drawing Sheets

(51) Int. Cl.
    *A61M 25/06* (2006.01)
    *A61B 17/34* (2006.01)
(52) U.S. Cl.
    CPC ........... *A61B 2017/3454* (2013.01); *A61M 2205/582* (2013.01); *A61M 2205/583* (2013.01)

(56) References Cited

U.S. PATENT DOCUMENTS

| | | | | |
|---|---|---|---|---|
| 4,973,313 | A * | 11/1990 | Katsaros | A61M 25/0606 604/165.02 |
| 5,186,712 | A * | 2/1993 | Kelso | A61M 25/0606 604/177 |
| 5,338,306 | A * | 8/1994 | Srivatsa | A61M 25/0606 604/165.02 |
| 5,755,709 | A * | 5/1998 | Cuppy | A61M 25/0606 604/167.03 |
| 6,641,555 | B1 * | 11/2003 | Botich | A61B 5/150389 604/110 |
| 2005/0090801 | A1 * | 4/2005 | Racz | A61M 25/0606 604/500 |
| 2007/0270758 | A1 * | 11/2007 | Hanner | A61M 25/0625 604/177 |
| 2011/0224617 | A1 | 9/2011 | Miner | |
| 2015/0343173 | A1 * | 12/2015 | Tobescu | A61M 25/0017 604/246 |
| 2017/0120011 | A1 | 5/2017 | Burkholz et al. | |

* cited by examiner

CATHETER DEVICE COMPRISING A LEVERING MEMBER

CROSS REFERENCE TO RELATED APPLICATIONS

This application is a § 371 National Stage Application of PCT/EP2020/078356 filed Oct. 9, 2020, which claims priority to SE 1951197-1 filed Oct. 23, 2019.

FIELD OF THE INVENTION

The present invention relates to a catheter device comprising a catheter and a hypodermic introducer needle. More specifically, the disclosure relates to a catheter device comprising a catheter and a hypodermic introducer needle as defined in the introductory parts of claim 1.

BACKGROUND ART

Intravascular catheter devices are known within the art and commonly used to provide access into subcutaneous blood vessels, such as veins, to introduce medication, drugs, chemotherapy, nutrition and/or any other fluids into a subject. SE 355946 discloses a basic type of infusion cannula assembly that is still widely used. The catheters are normally flexible or semi-flexible in order to be fitted within the blood vessel. As the flexible or semi-flexible catheter is incapable of piercing the skin of a subject, an introducer needle is inserted into the lumen of the catheter such that a beveled tip of the needle is exposed beyond the distal tip end of the catheter. By inserting the beveled tip of the needle through the skin and into the targeted blood vessel, the vasculature of a patient is accessed. The insertion into a blood vessel by the needle is indicated by the appearance of blood in a chamber in a needle head. Once the beveled tip of the needle is inserted into the blood vessel such that blood appears in said chamber, the catheter and the needle are advanced distally into the blood vessel until the desired position of the catheter is achieved. Once the catheter is properly positioned, the needle is removed by pulling the needle proximally from the catheter and the needle is thereafter discarded.

One common problem when inserting catheters is that once blood appears in the chamber, and the needle and catheter are further advanced distally, there is a risk of puncturing the blood vessel further and thereby exiting the blood vessel through an opposite blood vessel wall. This will lead to the catheter not being properly placed. However, this may be difficult to detect, and often leads to discomfort for the patient before being discovered. Once detected, the improperly positioned catheter must be discarded, and the entire procedure has to be repeated with a new catheter device, leading to great discomfort and additional pain for the patient, as well as a negative economic effect due to waste of medical material.

One common practice to avoid the above-mentioned problem is to "hood" the needle once the blood vessel has been accessed. "Hooding" involves maintaining a stationary position of the needle while simultaneously distally motioning the partially inserted catheter, such that the beveled needle tip is withdrawn into the inner lumen of the catheter. Once the beveled needle tip is hooded, the catheter device is advanced distally into the vein into a desired position.

One problem with this technique is when the beveled needle tip has just pierced the blood vessel enough for blood to appear in the needle chamber, but not completely entered the blood vessel. The hooding may then lead to the catheter sliding along the exterior of the blood vessel. Consequently, the catheter is not properly placed in the blood vessel. This will lead to a need to repeat the procedure, having the same consequences as stated above.

Furthermore, hooding is performed blindly as the user cannot see the subcutaneous position of the needle or the catheter in the blood vessel. The beveled needle tip may therefore be overhooded or underhooded. Underhooding means that a portion of the beveled needle tip is still exposed beyond the tip of the catheter, risking puncturing a blood vessel further such as mentioned above. Overhooding means that the beveled needle tip is overdrawn proximally into the lumen of the catheter, leaving the most distal end of the flexible or semi-flexible tip of the catheter unsupported by the needle. The unsupported portion of the catheter may then risk being bent, nicked, or otherwise obstructed while being advanced into the blood vessel. This may lead to insufficient administration of fluids and/or medication through the lumen.

Once the beveled needle tip is hooded and in a desired subcutaneous position, the beveled needle tip may not be pushed back distally into an exposed position where the beveled needle tip protrudes distally of the catheter tip end, as this may cause the beveled needle tip to cut off or tear off a part of the catheter tip end. Thus, when discovering that the catheter is not properly positioned after having hooded the beveled needle tip, the improperly positioned catheter must be discarded, and the entire procedure has to be repeated with a new catheter device, leading to great discomfort and additional pain for the patient, as well as a negative economic effect due to waste of medical material.

SUMMARY

It is an object of the present invention to mitigate, alleviate or eliminate one or more of the above-identified deficiencies and disadvantages in the prior art and solve at least the above-mentioned problem. The inventor has noticed all the problems listed above that may occur when inserting intravenous catheters. In particular, un-experienced users may have a high frequency of improperly positioned catheters. Thus, the inventor has identified an objective of developing an intravenous catheter device that may guide the user and control the insertion process of a catheter such that the problems above are avoided. Another objective of the inventor has been to develop an intravenous catheter device that is easy to use, and does not substantially change the practice compared to today. Additionally, the inventor has had as an objective to develop an intravenous catheter device that may be operated with one hand, making it possible to use one hand to, for instance, hold a limb of a patient while inserting the catheter with the other hand.

According to a first aspect there is provided a catheter device having an axis A-A, a lower side adapted to face a patient, and an upper side opposite the lower side adapted to face away from the patient, the catheter device comprising a catheter and a hypodermic introducer needle:

the catheter comprising an axially elongated housing having a proximal open end adapted to receive a coupling mechanism or a plug, the housing further comprising an internal passage, a connecting port with an internal orifice arranged on the upper side of the catheter, protrusion members on the outer surface of the proximal open end, and the catheter further comprising a flexible catheter tube connected to the elongated housing, the flexible catheter tube comprising a distal tip end and a lumen, the lumen being in fluid communication with the internal passage of the housing;

the introducer needle comprising a proximal head, a hollow needle having a distal beveled tip, an extended portion connecting the needle with the head and adapted to engage with the proximal end of the catheter when the needle is inserted into the catheter, the head comprising an axial channel in fluid communication with the interior of the hollow needle, a grip plate arranged on the head and extending in a direction perpendicular to the axial direction, and an engagement member arranged on the grip plate and protruding distally from the grip plate;

the catheter and needle being arranged such that when the needle is inserted into the catheter, the grip plate is directed towards the upper side of the catheter and aligned with the connection port, and wherein the protrusion members on the proximal end of the catheter are adapted to engage with the engagement member on the grip plate to prevent the needle from rotating around the axis A-A in relation to the catheter;

wherein the catheter device further comprises a levering member adapted to be removably attached to the catheter and further adapted to motion the catheter from a retracted proximal position to an advanced distal position in the axial direction in relation to the introducer needle, wherein in the retracted proximal position the beveled tip of the introducer needle protrudes from the distal end of the catheter tube, and wherein in the advanced distal position the beveled tip of the introducer needle is hooded by the catheter tube, the catheter device further comprising visual and/or tactile indicators on the grip plate and/or on the extended portion to indicate at least the advanced positions of a) the catheter being advanced a distance d, the distance d corresponding to the length of the beveled tip of the needle, and optionally b) the catheter being advanced a distance D, the distance D corresponding to a length greater than the length of the beveled tip of the needle, such as twice the length of the beveled tip, or more.

According to some embodiments, the levering member comprises a levering arm and a connector for connecting with the catheter.

According to some embodiments, the levering member interacts with the grip plate of the introducer needle to motion the catheter to advance distally.

According to some embodiments, said connector further comprises engagement recesses adapted to engage with the protrusions on the proximal end of the catheter to removably connect the levering member to the catheter.

According to some embodiments, the levering member is adapted to be removably attached to the connecting port of the catheter. According to some embodiments, the length of the extended portion of the needle is at least equal to, or larger than the total length that the levering member will advance the catheter when fully advanced.

According to some embodiments, the indicators comprise stop surfaces arranged on the grip plate such that the levering member will engage with said stop surfaces, providing a tactile indication for the user.

According to some embodiments, the stop surfaces comprise grooves, protrusions or edges arranged on the grip plate.

According to some embodiments, the levering arm comprises an interacting member adapted to interact with the stop surfaces of the grip plate.

According to some embodiments, the levering arm has an L-like shape, or a curved shape, and is arranged on the catheter such that the interacting member comprises an angle of the L-like shape, or a convex surface of the curved shape, or a ridge on said convex surface, adapted to engage with the stop surfaces of the grip plate.

According to some embodiments, the indicators are arranged on the extended portion of the needle.

According to some embodiments the extended portion of the needle is provided with ribs that circumvent the extended portion radially from the axis A-A, and the proximal end of the catheter or the connector of the levering member is provided with a locking flange, adapted to engage with the ribs on the extended portion of the needle when the catheter is motioned distally in relation to the needle, the ribs optionally being marked in order to indicate the position of the beveled tip of the needle in relation to the distal end of the catheter tube.

According to some embodiments, the extended portion of the needle comprises a chamfered surface along one side of the entire extended portion, leading to a cross-sectional U-shape of the extended portion.

According to some embodiments the indicators comprises marking of a rib that will correspond to the catheter being advanced a specified distance, providing a visual indication for the user, in addition to a tactile indication provided by each rib being pulled over and engaging with the locking flange.

According to some embodiments, the levering arm comprises a lug and the elongated house of the catheter or optionally the proximal end of the connector of the levering member comprises a retainment element, said retainment element being adapted to engage with the lug such that the levering member reversibly locks the catheter device in a fully advanced position.

According to a second aspect there is provided a levering member adapted to be connected to a catheter, said levering member comprising a levering arm adapted to engage with a grip plate of an introducer needle inserted into the catheter, and a connector adapted to be removably attached to the catheter.

According to some embodiments, the connector further comprises engagement recesses adapted to engage with protrusions on a proximal end of the catheter to removably connect the levering member to the catheter.

According to some embodiments, said connector is adapted to engage with the connecting port of the catheter to removably connect the levering member to the catheter.

According to some embodiments, the levering arm comprises a protruding lug adapted to engage with a retainment element, said retainment element being arranged on the connector of the levering member or arranged on the proximal end of the catheter.

According to a third aspect there is provided a catheter device according to the first aspect for use in placing a catheter in a blood vessel in a patient, comprising the steps of:

i. positioning the catheter device against the skin of the patient, in the location where the catheter is to be placed, and advancing the catheter device by a distal motion towards a subcutaneous blood vessel, ii. stopping the distal motion when blood appears in the head of the introducer needle, indicating that a blood vessel has been entered, iii. motioning a levering member towards the grip plate while keeping the introducer needle still, iv. pressing the levering member against the grip plate, thereby causing the levering member to glide against the grip plate towards the elongated housing, further causing the catheter to move distally in relation to the introducer needle that is kept still, until a first indicator is reached, indicating that the beveled tip of the introducer needle is hooded, v. further motioning the catheter device into the blood vessel, vi. further motioning the levering member, while keeping the introducer needle still, to further distally advance the catheter into the blood vessel, in one or optionally more than one steps, vii. attaching the catheter against the skin of the patient by attachment members upon full advancement of the catheter in relation to the introducer needle by use of the levering member, viii. removing the introducer needle and the levering member from the catheter device, and sealing the proximal open end of the catheter by use of a removable plug or by connection to an infusion device or the like.

Herein is also provided a method for placing a catheter in a blood vessel in a patient, comprising the steps of:

i. positioning a catheter device, comprising a catheter and an introducer needle, against the skin of the patient, in the location where the catheter is to be placed and advancing the catheter device by a distal motion towards a subcutaneous blood vessel, ii. stopping the distal motion when blood appears in the head of the introducer needle, indicating that a blood vessel has been entered, iii. motioning a levering member towards a grip plate on the introducer needle, while keeping the introducer needle still in relation to the patient, iv. pressing the levering member against the grip plate, thereby causing the levering member to glide against the grip plate towards the elongated housing, further causing the catheter to move distally in relation to the introducer needle that is kept still, until a first indicator is reached, indicating that the beveled tip of the introducer needle is hooded, v. further motioning the catheter device into the blood vessel, vi. further motioning the levering member, while keeping the introducer needle still, to further distally advance the catheter into the blood vessel, in one or optionally more than one steps, vii. attaching the catheter against the skin of the patient by attachment members upon full advancement of the catheter in relation to the introducer needle by use of the levering member, viii. removing the introducer needle and the levering member from the catheter device, and sealing the proximal open end of the catheter by use of a removable plug or by connection to an infusion device or the like.

The present invention will become apparent from the detailed description given below. The detailed description and specific examples disclose preferred embodiments of the invention by way of illustration only. Those skilled in the art understand from guidance in the detailed description that changes and modifications may be made within the scope of the invention.

Hence, it is to be understood that the herein disclosed invention is not limited to the particular component parts of the device described or steps of the methods described since such device and method may vary. It is also to be understood that the terminology used herein is for purpose of describing particular embodiments only, and is not intended to be limiting. It should be noted that, as used in the specification and the appended claim, the articles "a", "an", "the", and "said" are intended to mean that there are one or more of the elements unless the context explicitly dictates otherwise. Thus, for example, reference to "a unit" or "the unit" may include several devices, and the like. Furthermore, the words "comprising", "including", "containing" and similar wordings does not exclude other elements or steps.

DEFINITIONS

The term "user" is to be interpreted as a caregiver who is to perform placement of catheters or perform other medical treatments, preparations, operations, etc. on a patient.

The term "distal" is to be interpreted as referring to a position or location away from the user. The term "distally" is to be interpreted as referring to a motion leading away from the user.

The term "proximal" is to be interpreted as referring to a position or location close to user. The term "proximally" is to be interpreted as referring to a motion leading towards the user.

The terms "vessel" or "blood vessel" are to be interpreted as any vessel within a patient. It may relate to an artery or a vein.

The term "bevel angle" is herein discussed as one angle. However, a beveled needle tip may comprise more than one angled surface, such as heel of bevel and secondary bevel. What is important for the understanding of the present disclosure is that the term "bevel length" encompasses the entire bevel length, comprising all beveled surfaces of the needle tip.

DETAILED DESCRIPTION

The above objects, as well as additional objects, features and advantages of the present invention will be more fully appreciated by reference to the following illustrative and non-limiting detailed description of example embodiments of the present invention, when taken in conjunction with the accompanying drawings.

The catheter device according to the present disclosure has an axis A-A, a lower side adapted to face a patient, and an upper side opposite the lower side adapted to face away from the patient. The catheter device comprises a catheter and a hypodermic introducer needle.

The catheter comprises an axially elongated housing having a proximal open end adapted to receive a coupling mechanism or a plug. The proximal end may for instance be provided with a female Luer Lock fitting as a coupling mechanism, for easy fitting with syringes etc. Through the coupling mechanism, the catheter may be coupled to an infusion device or any other medical equipment that is common to connect with a catheter. The housing further comprises an internal passage, a connecting port with an internal orifice arranged on the upper side of the catheter. The connecting port may for instance be used for injecting drugs or pharmaceuticals into an infusion liquid being perfused into a patient via the catheter. The housing further comprises protrusion members on the outer surface of the proximal open end in order to engage with and lock the plug or coupling mechanism disclosed above. The catheter further comprises a flexible catheter tube connected to the elongated housing, the flexible catheter tube comprising a distal tip end and a lumen, the lumen being in fluid communication with the internal passage of the housing. The flexible catheter tube is the part of a catheter that is placed in a blood vessel, and must be flexible in order to not injure or puncture the blood vessel into which it is inserted.

The introducer needle comprises a proximal head, a hollow needle having a distal beveled tip and an extended portion connecting the needle with the head. The extended portion is adapted to engage with the proximal end of the catheter when the needle is inserted into the catheter. The head comprises an axial channel in fluid communication with the interior of the hollow needle, and a grip plate arranged on the head and extending in a direction perpendicular to the axial direction and an engagement member arranged on the grip plate and protruding distally from the grip plate.

The catheter and the introducer needle, apart from the hypodermic hollow needle, are typically manufactured by a synthetic polymer material that is transparent or semi transparent. Typically, the material for manufacturing may be a polyurethane, or polytetrafluoroethylene such as fluorinated ethylene propylene (FEP). The hypodermic hollow needle is normally manufactured of stainless steel, said steel optionally being plated.

The catheter and needle are arranged such that when the needle is inserted into the catheter, the grip plate is directed towards the upper side of the catheter and aligned with the connection port. Furthermore, the protrusion members on the proximal end of the catheter are adapted to engage with the engagement member on the grip plate to prevent the needle from rotating around the axis A-A in relation to the catheter.

The catheter device further comprises a levering member adapted to be removably attached to the catheter and further adapted to motion the catheter from a retracted proximal position to an advanced distal position in the axial direction in relation to the introducer needle. In the retracted proximal position, the beveled tip of the introducer needle protrudes from the distal end of the catheter tube. In the advanced distal position, the beveled tip of the introducer needle is hooded by the catheter tube. The catheter device further comprises indicators to indicate at least the advanced positions of a) the catheter being advanced a distance d, the distance d corresponding to the length of the beveled tip of the needle, and optionally b) the catheter being advanced a distance D, the distance D corresponding to a length greater than the length of the beveled tip of the needle, such as twice the length of the beveled tip, or more. The device may comprise additional indicators correlating to other distances that are advantageous to indicate during the use of the catheter device according to the present disclosure.

The catheter device is initially used in the same manner as traditional catheter devices. Thus, the catheter device is positioned against the skin of a patient, keeping the axis A-A almost in parallel with the skin surface, slightly tilted so that the distal beveled tip of the introducer needle is in contact with the skin, while the proximal end of the catheter and the head of the introducer needle is kept at a small height from the skin surface. Thereafter the catheter device is advanced distally so that the distal beveled tip perforates the skin and eventually also perforates a target blood vessel. The user will know that a blood vessel has been perforated by the distal beveled tip as blood will enter the introducer needle and appear in the axial channel of the head of the needle. Thus, the user will visually observe blood appearing in the head of the needle through the transparent or semi-transparent material.

Once blood enters axial channel, the levering member is motioned to a first indicator, whereby the catheter is motioned from a retracted proximal position to an advanced distal position in relation to the needle. Motioning the levering member to the position of the first indicator means that the catheter has been advanced a distance d in relation to the needle, where the distance d is equal to the length of the distal beveled tip of the needle. Hence, the distal beveled tip of the needle has been hooded by the catheter tip end. At this point of the procedure, the beveled tip of the needle may not be motioned distally to protrude from the distal tip end of the catheter, as this may cause the beveled tip to cut or tear off a small piece of the catheter tube. Thus, reaching the first indicator with the levering member is also a point of no return for the catheter device. If anything is discovered to be incorrect in connection with the placement of the catheter, the entire catheter device must be discarded. A levering member may possibly be removed from the catheter device and reused with a new catheter device, under the provision that the levering member has not been in any contact with blood or any other body fluid.

After the above described hooding is performed, the catheter device is further motioned distally into the blood vessel. Thereafter the levering member is further motioned to a second indicator, whereby the catheter is motioned from a first advanced distal position to a second advanced distal position in relation to the needle. Motioning the levering member to the position of the second indicator means that the catheter has been advanced a distance D in relation to the needle. The distance D is equal to a length exceeding the length of the distal beveled tip of the needle, such as twice the length ($2x$) of the distal beveled tip, or more. This action will thus ensure that the catheter tube is well inserted into the blood vessel, beyond the distal beveled tip of the introducer needle.

In the case where the beveled tip has partially but not fully entered the vessel in the first step, the hooding will forward the catheter to the same position as the point of the beveled tip within the vessel, and the further advancement of the catheter device into the vessel will position the catheter tip further in the vessel, without risking piercing the vessel on an opposite side with a beveled tip protruding from the catheter tip.

The length of the beveled tip, and hence the distances d and D, is dependent on the gauge of the needle being used. A high gauge corresponds to a needle with a smaller diameter, whereas a low gauge corresponds to a needle with a larger diameter. The larger the diameter of a needle, the longer is the length of the beveled tip. The length of the beveled tip will also depend on a bevel angle of the needle tip. Hence, the indicators are adapted for the gauge and bevel angle of the needle intended to be used. The skilled person within the present technical field will be able to determine the lengths and distances for each gauge and bevel angle, and consequently be able to place the indicators such that said lengths and distances are indicated according to the present disclosure.

All handling during placement of a catheter may be done with one hand using the device of the present disclosure, from piercing of the skin to hooding of the beveled tip of the needle. While holding the catheter device with the one hand, pulling the levering member entails an intuitive action by the user and can be done with one finger on the same hand. Thus, the user may use the other hand to hold a patients limb, to stretch the skin before piercing said skin, etc.

The catheter device disclosed herein provides clear indications of when the beveled tip is hooded and overhooded, respectively. The indications may be visual and/or tactile. Thus, the process of placing a catheter is no longer performed blindly by use of the presently disclosed device. The user will always be certain that once the first indicator is reached with the levering member, the beveled tip of the needle is hooded and hence the risk of further piercing of any tissue is reduced.

The levering member may comprise a levering arm and a connector for connecting with the catheter. The levering arm must be adapted to be actuated such that the catheter is motioned distally in relation to the introducer needle, where the actuation of the levering arm will not cause the introducer needle to be motioned in any direction, neither distally nor proximally. Providing the levering member with a levering arm enables an intuitive actuation by the user in pulling the levering arm proximally to advance the catheter distally. The levering arm preferably comprises an L-like shape, or a curved shape.

The levering member may interact with the grip plate of the introducer needle to motion the catheter to advance distally. Thus, the levering member, or optionally the levering arm, is preferably proximally motioned to interact with the grip plate, which is positioned on the introducer needle and in a proximal position in relation to both the levering member and the catheter. Thus, the grip plate provides a resistance against which the levering members applied input force be directed. This causes the levering members output force to be exerted against the catheter at the point at which the levering member is attached or connected to the catheter, motioning the catheter in a direction away from the grip plate, i.e. distally. Consequently, the levering function of the levering member is enhanced.

As mentioned above, the levering member may comprise a connector. The connector may comprise engagement recesses adapted to engage with the protrusions on the proximal end of the catheter, to removably connect the levering member to the catheter. The engagement of the engagement recesses to said proximal protrusions further prevents the levering member from rotating around the axis A-A. Thereby it is ensured that the levering member and optionally the levering arm are aligned with the connection sleeve of the catheter and with the grip plate of the needle. Thus, the levering member may interact with the grip plate as disclosed above.

The levering member may alternatively be adapted to be removably attached to the connecting port of the catheter. Thus, the connector is adapted to at least partially enclose or encircle an outer circumference of the connecting port, directly adjacent to the elongated housing, so as to not prevent a plug from being able to be fitted on the connecting port. Preferably the connector does not completely enclose or encircle the connecting port, in order to be more easily removable from the connecting port, regardless of whether the connecting port is fitted with a plug or not. Once the levering member has been removably attached to the connecting port, a plug fitted on the connecting port may help in keeping the levering member in place. However, this is not essential for the function of the levering member.

The levering member may easily be removed together with the needle once the catheter has been properly positioned. As the levering member is motioned towards the grip plate of the introducer needle during placement of the catheter, it is easy to simply grip the levering member and the grip plate simultaneously and remove both from the catheter by pulling both items proximally until they exit the catheter. Thus, there is no extra step needed to remove the levering member from the catheter. Both a levering member removably attached to the proximal end of the catheter, as well as a levering member removably attached to the connection port, may be removed accordingly.

The length of the extended portion of the needle may preferably be at least equal to, or larger than, the total length that the levering member may advance the catheter. This will provide stability during handling of the catheter device and in particular, during the removal of the introducer needle once the catheter has been properly positioned in a blood vessel. Thus, when the catheter tube is advanced distally over the needle, and when the needle is further pulled back proximally and removed from the catheter, the needle will not risk wobbling or moving in a direction that is perpendicular to the axis A-A. Thereby, the risk of damaging the catheter tube during the removal of the needle is minimized. Further, the handling of the needle by the user placing the catheter is rendered stable and secure.

The indicators may comprise stop surfaces. The stop surfaces may be arranged on the grip plate such that the levering member will engage with said stop surfaces, providing a tactile indication for the user. Stop surfaces arranged on the grip plate are placed at different distances from the central A-A axis on the distal surface of the grip plate. The first indicator stop surface will be placed at a longer distance from the central A-A axis than a second indicator stop surface. Thereby, the levering member will first engage with the first indicator stop surface when being motioned towards the grip plate. Further motioning the levering member proximally will cause the levering member to glide along the grip plate towards the central A-A axis of the catheter device and engage with the second indicator stop surface.

The stop surfaces may comprise grooves, protrusions or edges arranged on the grip plate. The specific shape of the stop surfaces is not crucial. The stop surfaces are provided at predetermined locations on the grip plate, where said locations during handling of the catheter device as described in the present disclosure will correspond to the catheter being advanced at least the distances d and optionally D.

The levering arm may comprise an interacting member adapted to interact with the stop surfaces of the grip plate. As disclosed above, the levering arm preferably has an L-like shape, or a curved shape. The interacting member may preferably comprise an outer angle of the L-like shape, or a convex surface of the curved shape, or a ridge on said convex surface, adapted to engage with the stop surfaces of the grip plate. However, the skilled person will acknowledge that further shapes are possible which will provide the function as disclosed herein for the levering member.

The extended portion of the needle may be provided with ribs that circumvent the extended portion radially from the axis A-A. In this embodiment, the proximal end of the catheter or optionally the connector of the levering member is provided with a locking flange, adapted to engage with the ribs on the extended portion of the needle when the catheter is motioned distally in relation to the needle. For each rib engaging with the locking flange, a tactile indication is being provided to the user. Additionally, the ribs engaging with the locking flange will prevent the needle from being motioned back into the catheter. This embodiment of the extended portion may be combined with any levering member disclosed herein.

Once the beveled tip of the needle is hooded by the catheter tip end as disclosed above, the ribs on the extended portion have engaged with the locking flange, thereby preventing any distal motion of the needle in relation to the catheter. It is thus at this stage possible to further advance the entire catheter device by merely pushing the needle distally. Due to the engagement of the ribs with the locking flange, there is no risk of the needle protruding the catheter tip end by pushing the needle. Thereby, there is little or no risk of the beveled tip cutting off a part of the catheter tip end. The indicators may alternatively or additionally be arranged on the extended portion of the needle. Thus, the extended portion of the needle may be provided with ribs that circumvent the extended portion radially from the axis A-A, as disclosed above, and said ribs may be marked in order to indicate the position of the beveled tip of the needle in relation to the distal end of the catheter tube. The indicators thus comprises marking of a rib that will correspond to the catheter being advanced a specified distance, providing a visual indication for the user, in addition to a tactile indication provided by each rib being pulled over and engaging with the locking flange. The marking of a rib may comprise a symbol, letter, number or colour of a specific rib. Thus, a rib which upon engagement with the locking flange will result in the catheter being motioned distally a distance d, and a rib which upon engagement with the locking flange will result in the catheter being motioned distally a distance D, may be marked. The markings may be the same or different. The first marking being located most proximal on the introducer needle, and closest to the grip plate, will indicate a distance d, and any further markings being located more distally, and farther from the grip plate, will indicate one or more distances D.

The extended portion of the needle being provided with ribs according any of the embodiments above, may further comprise a chamfered surface along one side of the entire extended portion, leading to a cross-sectional U-shape of the extended portion. Thereby a rotation of the needle will enable re-entry of the needle into the catheter, as the flat chamfered surface of the extended portion will not engage with the locking flange. Thus, the needle may be re-advanced into the catheter. This may be useful if an introducer needle is removed from the catheter by accident. However, more importantly, this is crucial for being able to introduce the introducer needle into the catheter at assembly of the catheter device. However, rotation of the needle to reinsert the needle into the catheter must never be done if the catheter device is already inserted into a patient, for the reasons given above in the present disclosure.

The levering arm may comprise a lug and the elongated house of the catheter or optionally the proximal end of the connector of the levering member may comprise a retainment element. Said retainment element is adapted to engage with the lug such that the levering member reversibly locks the catheter device in a fully advanced position. It is feasible to design this locking arrangement with other features than a lug and a retainment element as disclosed herein, while retaining the same function.

Thus, a levering member adapted to be connected to a catheter has been disclosed herein, said levering member comprising a levering arm adapted to engage with a grip plate of an introducer needle inserted into the catheter, and a connector adapted to be removably attached to the catheter. Said levering member may display all or some of the features disclosed above for a levering member. Thus, the connector may further comprise engagement recesses adapted to engage with protrusions on a proximal end of the catheter, in order to removably connect the levering member to the catheter as disclosed above. Alternatively, said connector may be adapted to engage with the connecting port of the catheter, in order to removably connect the levering member to the catheter as disclosed above. The levering arm may comprise a protruding lug adapted to engage with a retainment element, said retainment element being arranged on the connector of the levering member or arranged on the proximal end of the catheter.

The levering member may be provided individually for the user to connect the levering member to a catheter device, or the catheter device may be provided with the levering member at the manufacturing thereof.

The manufacture and packaging of the levering member and/or the catheter device according to the present disclosure should be in accordance with regulatory rules and guidelines for use in the healthcare system. Any device that is intended to be used within healthcare and come in contact with a patient and/or bodily fluids must follow such regulatory rules and guidelines.

According to the present disclosure, a catheter device according to the above is provided, for use in placing a catheter in a blood vessel in a patient, comprising the steps of:

i. positioning the catheter device against the skin of the patient, in the location where the catheter is to be placed, and advancing the catheter device by a distal motion towards a subcutaneous blood vessel, ii. stopping the distal motion when blood appears in the head of the introducer needle, indicating that a blood vessel has been entered, iii. motioning the levering member towards the grip plate while keeping the introducer needle still in relation to the patient, iv. pressing the levering member against the grip plate, thereby causing the levering member to glide downwards against the grip plate, causing the catheter to move further distally in relation to the introducer needle that is kept still, until a first indicator is reached, indicating that the beveled tip of the introducer needle is hooded, v. further motioning the catheter device into the blood vessel, vi. further motioning the levering member, while keeping the introducer needle still, to further distally advance the catheter into the blood vessel, in one or optionally more than one steps, vii. attaching the catheter against the skin of the patient upon full advancement of the catheter in relation to the introducer needle by use of the levering member, viii. removing the introducer needle and the levering member from the catheter device, and sealing the proximal open end of the catheter by use of a removable plug or by connection to an infusion device or the like.

Provided herein is also a method for placing a catheter in a blood vessel in a patient, comprising the steps of:

i. positioning a catheter device according to the present disclosure against the skin of the patient, in the location where the catheter is to be placed, and advancing the catheter device by a distal motion towards a subcutaneous blood vessel, ii. stopping the distal motion when blood appears in the head of the introducer needle, indicating that a blood vessel has been entered, iii. motioning the levering member towards the grip plate of the introducer needle, while keeping the introducer needle still in relation to the patient, iv. pressing the levering member against the grip plate, thereby causing the levering member to glide downwards against the grip plate, causing the catheter to move further distally in relation to the introducer needle that is kept still, until a first indicator is reached, indicating that the beveled tip of the introducer needle is hooded, v. further motioning the catheter device into the blood vessel, vi. further motioning the levering member, while keeping the introducer needle still, to further distally advance the catheter into the blood vessel, in one or optionally more than one steps, vii. attaching the catheter against the skin of the patient upon full advancement of the catheter in relation to the introducer needle by use of the levering member, viii. removing the introducer needle and the levering member from the catheter device, and sealing the proximal open end of the catheter by use of a removable plug or by connection to an infusion device or the like.

Attachment of the catheter to the skin of a patient is preferably done by attaching attachment members to the skin. The attachment member may for instance be wing-like structures arranged on the lower side of a catheter.

The present invention will now be described with reference to the accompanying drawings, in which preferred example embodiments of the invention are shown. The invention may, however, be embodied in other forms and should not be construed as limited to the herein disclosed embodiments. The disclosed embodiments are provided to fully convey the scope of the invention to the skilled person.

Arrangement and design for stop surfaces and interacting member are mostly shown for the embodiment where the connector of the levering member is attached to the proximal end of the elongated housing, but is not limited to those drawings. It is possible to combine also with the embodiment where the connector is attached to the connecting port.

Figure 1A:
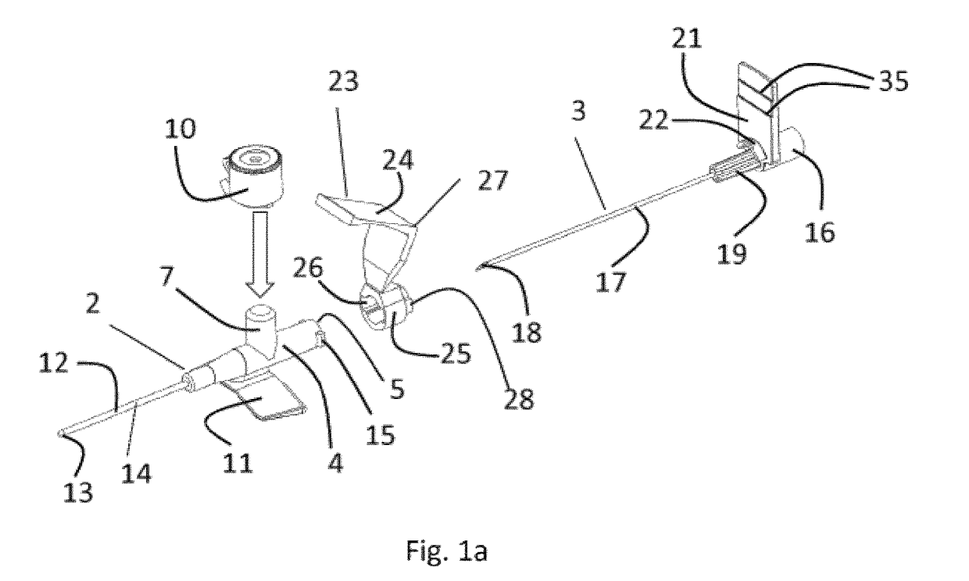
FIG. 1a shows a perspective view of the parts comprised in the catheter device according to an embodiment of the present disclosure.
Figure 1B:
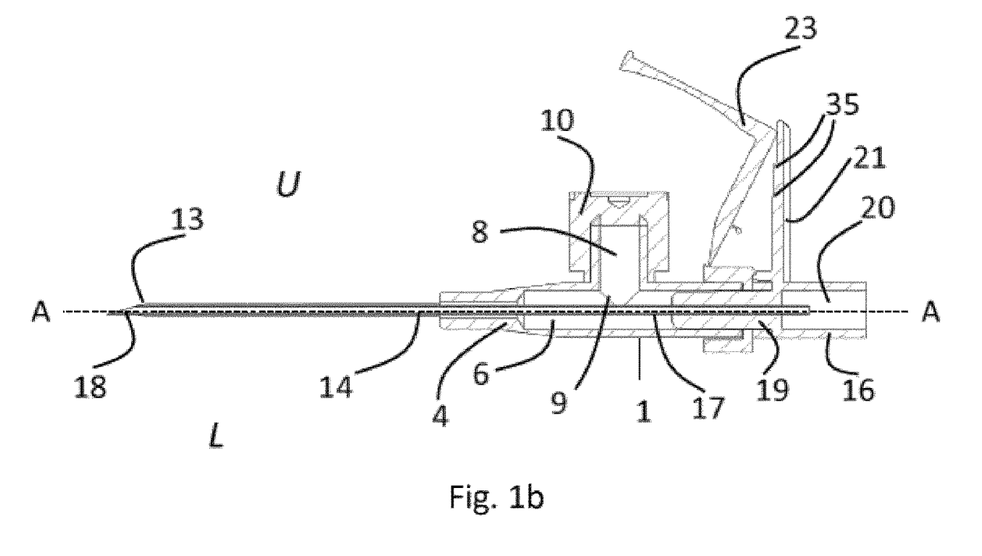
FIG. 1b shows a cross-sectional view of the catheter device as shown in FIG. 1a upon assembly.

FIGS. 1a and 1b show one embodiment of the catheter device 1, having a central axis A-A, a lower side (L) adapted to face a patient, and an upper side (U) opposite the lower side (L) adapted to face away from the patient, the catheter device 1 comprising a catheter 2 and a hypodermic introducer needle 3. The catheter 2 comprises an axially elongated housing 4 having a proximal open end 5 adapted to receive a coupling mechanism or a plug. The housing 4 further comprises an internal passage 6, a connecting port 7 with an internal orifice 8 arranged on the upper side of the catheter, said orifice 8 being in connection with the internal passage 6 by a non-return valve 9. A plug 10 may be fitted over the connecting port 7. Protrusion members 15 are arranged on the outer surface of the proximal open end 5. The catheter 2 further comprises a flexible catheter tube 12 connected to the elongated housing 4, the flexible catheter tube 12 comprising a distal tip end 13 and a lumen 14, wherein the lumen 14 is in fluid communication with the internal passage 6 of the housing 4. In the present embodiment, catheter 2 further comprises attachment members 11, for attaching the catheter 2 to the skin of a patient. The introducer needle 3 comprises a proximal head 16, a hollow needle 17 having a distal beveled tip 18, an extended portion 19 connecting the needle 17 with the head 16 and adapted to engage with the proximal end 5 and the elongated housing 4 of the catheter 2 when the needle 3 is inserted into the catheter 2. The head 16 comprises an axial channel 20 in fluid communication with the interior of the hollow needle 17, a grip plate 21 arranged on the head 16 extending in a direction perpendicular to the axial direction of the catheter device 1, and an engagement member 22 arranged on the grip plate 21 and protruding distally from the grip plate 21. The catheter 2 and needle 3 are arranged such that when the needle 3 is inserted into the catheter 2, the grip plate 21 is directed towards the upper side of the catheter 2 and aligned with the connection port 7. The protrusion members 15 on the proximal end 5 of the catheter 2 are typically adapted to engage with the engagement member 22 on the grip plate 21 to prevent the needle 3 from rotating around the axis A-A in relation to the catheter 2.

The catheter device 1 further comprises a levering member 23 adapted to be removably attached to the catheter 2 and further adapted to motion the catheter 2 from a retracted proximal position to an advanced distal position in the axial direction in relation to the introducer needle 3. The levering member 23 comprises a levering arm 24 and a connector 25 for connecting with the catheter 2. As shown in FIG. 1b, the levering member 23 interacts with the grip plate 21 of the introducer needle 3 to motion the catheter 2 to advance distally. The connector 25 further comprises engagement recesses 26 adapted to engage with the protrusions 15 on the proximal end 5 of the catheter 2 to removably connect the levering member 23 to the catheter 2. The connector 25 furthermore comprises locking protrusion members 28, arranged proximally on said connector, and adapted to engage with the engagement member 22 on the introducer needle. Thus, the protrusion members 15 on the catheter 2 engage with the engagement recess 26 of the connector 25, and the locking protrusion members 28 of the connector 25 engage with the engagement member 22 on the grip plate 21 of the needle 3. This arrangement will ensure that all main units comprised in the catheter device 1, namely the catheter 2, the introducer needle 3, and the levering member 23, will be locked such that there will be no rotation around the A-A axis for of any of the said units in relation to each other.

Figure 2A:
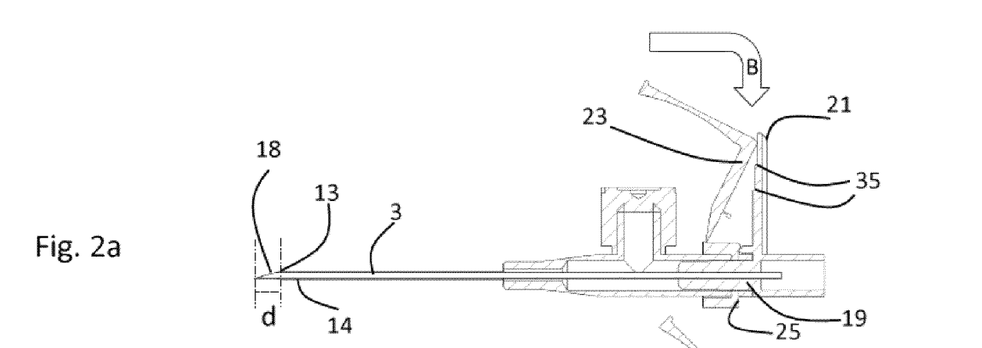
FIGS. 2a-c show cross-sectional views of the catheter device, illustrating the function of the levering member, according to an embodiment of the present disclosure.
Figure 2B:
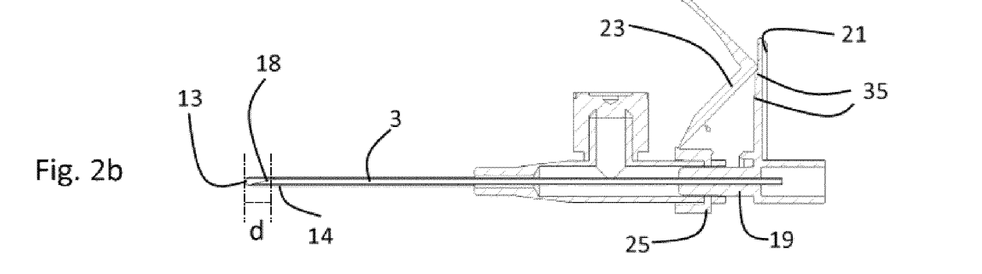
Figure 2C:
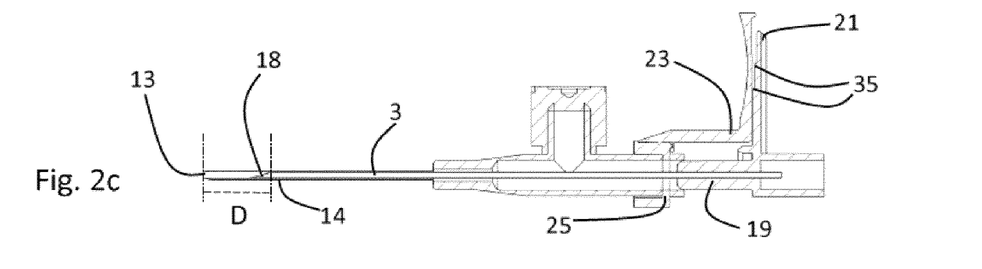

FIGS. 2a-c further illustrates the function of the levering member. In FIG. 2a, the catheter 2 is in the retracted proximal position, where the beveled tip 18 of the introducer needle 3 protrudes a length d from the distal end 13 of the catheter tube 12. In FIG. 2b, the levering member 23 has been motioned as indicated by the arrow B in FIG. 2a, to a first indicator stop surface 35 on the grip plate 21, leading to a first advanced distal position corresponding to hooding of the beveled tip 18 by the catheter tube 12. Thus, the catheter tube 12 has been advanced a distance d in relation to the introducer needle. In FIG. 2c, the levering member 23 has been fully motioned along the grip plate 21, leading to a fully advanced distal position wherein the catheter tube 14 has been advanced a distance D in relation to the introducer needle 3.

FIG. 2c further illustrates an embodiment where the length of the extended portion 19 of the needle 3 is at least equal to, or larger than the total length D that the levering member 23 will advance the catheter 2 when fully advanced.

Figure 3A:
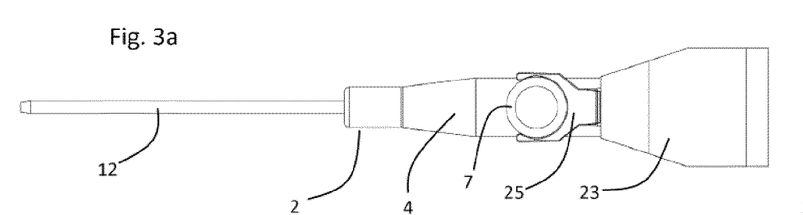
FIGS. 3a and 3b show a top view of the catheter device according to an embodiment of the present disclosure. 3a illustrates the catheter with a levering member, and 3b illustrates the catheter with a levering member and the introducer needle inserted into the catheter.
Figure 3B:
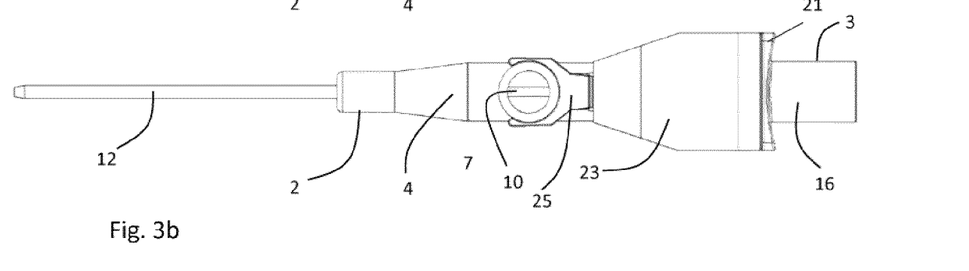

FIG. 3a illustrates an embodiment where the levering member 23 is removably attached to the connecting port 7 arranged on the elongated housing 4 of the catheter 2. FIG. 3b illustrates the same embodiment, including an introducer needle 3, where a plug 10 has been positioned on the connecting port 7, and the levering member 23 is fully motioned towards the grip plate 21 of the needle 3. Thus, the head 16 of the introducer needle 3 is visible proximally of the catheter 2, as the catheter 2 has been fully advanced in relation to the needle 3, such that the beveled tip (not shown) is overhooded by the catheter tube 12.

Figure 4A:
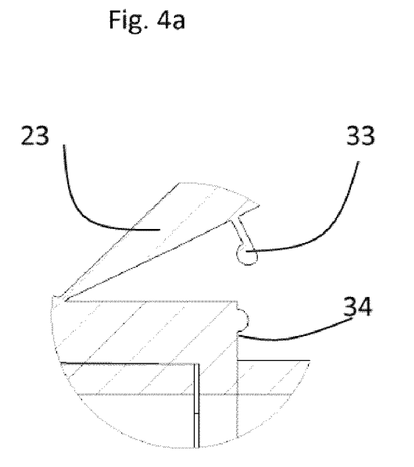
FIGS. 4a and 4b show a cross-sectional view of a retainment arrangement between the catheter and the levering member according to an embodiment of the present disclosure.
Figure 4B:
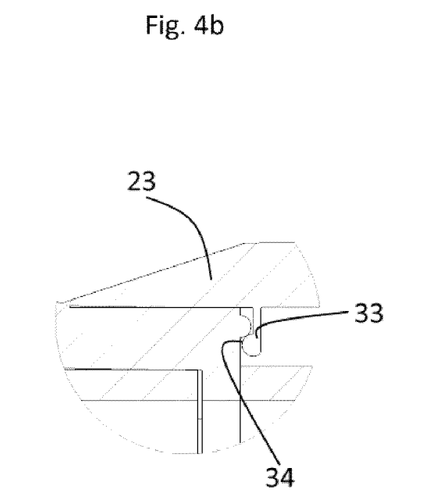

FIG. 4a illustrates an embodiment wherein the levering arm 24 of the levering member 23 comprises a lug 33 and the proximal end of the connector 25 of the levering member 23 comprises a retainment element 34. The retainment element 34 is adapted to engage with the lug 33 as shown in FIG. 4b such that the levering member 23 may be reversibly locked in a position where the catheter is fully advanced. The retainment element may be arranged on the elongated housing 4 of the catheter 2. This is preferred when the levering member 23 is connected to the connection port.

FIGS. 5a-f illustrates different non-limiting embodiments of the levering member 23, comprising different versions for the levering arm 24, interacting members 27, grip plate 21, and stop surfaces 35.

Figure 5A:
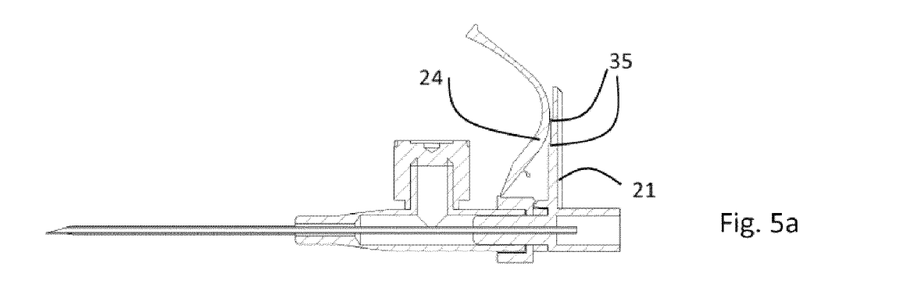
FIGS. 5a-f show cross-sectional views of other embodiments of the present disclosure.
Figures 5B, 5C:
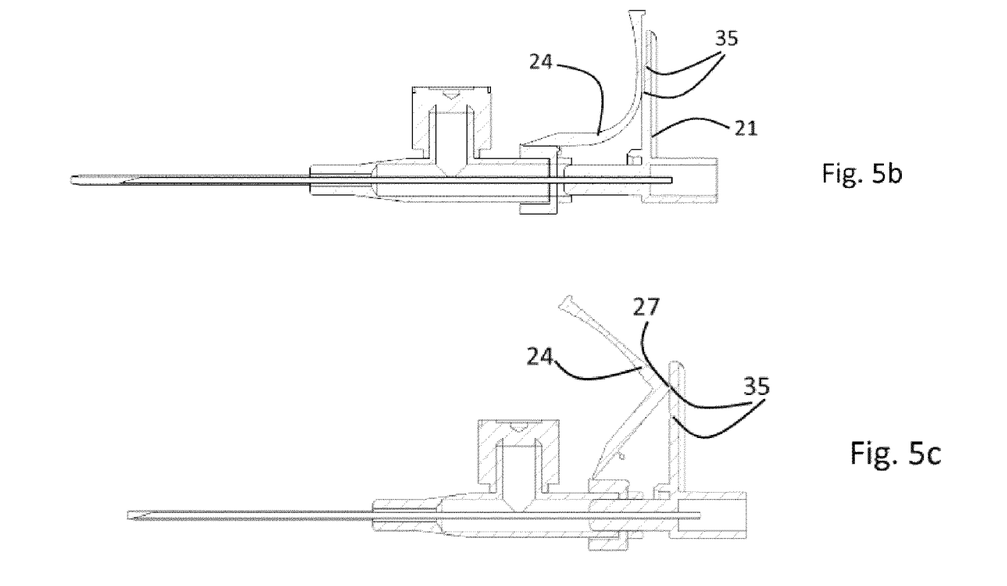

FIGS. 5a and 5b illustrates an embodiment of the catheter device wherein the levering arm 24 has a curved shape, and a convex surface of the levering arm 24 engages with stop surfaces 35 in the shape of edges on the grip plate 21.

FIG. 5c illustrates an embodiment where the levering arm 24 has an L-like shape, and an outer angle of the L-like shape acts as an interacting member 27 and engages with the stop surfaces 35 in the shape of grooves in the grip plate 21.

Figure 5D:
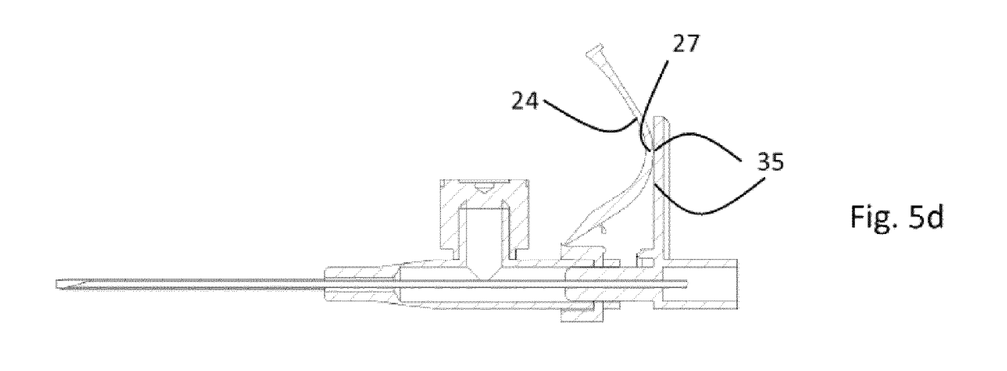

FIG. 5d illustrates an embodiment where the levering arm 24 has a curved shape, and a convex surface is provided with an interacting member 27 in the shape of a ridge. Said ridge engages with the stop surfaces 35 in the shape of grooves in the grip plate 21.

Figure 5E:
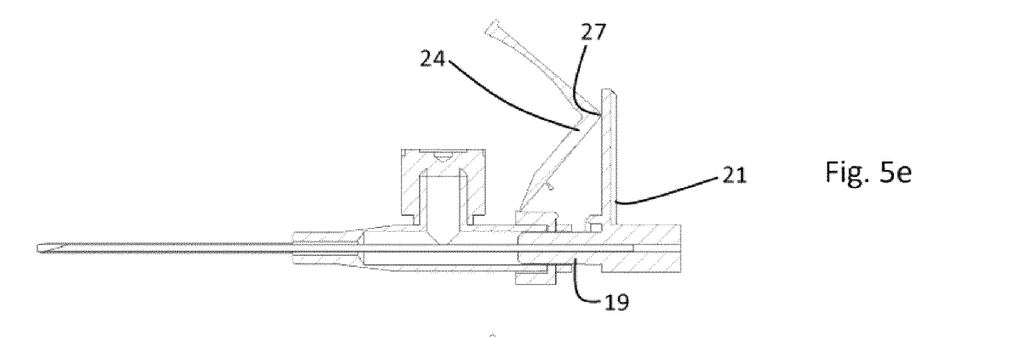

FIG. 5e illustrates an embodiment where the levering arm 24 has an L-like shape, and an outer angle of the L-like shape acts as an interacting member 27. In this embodiment the grip plate 21 does not comprise any stop surfaces. Such an embodiment may be provided with visual indicators (not shown) on the grip plate 21 and/or alternatively visual and/or tactile indicators (not shown) on the extended portion 19.

Figure 5F:
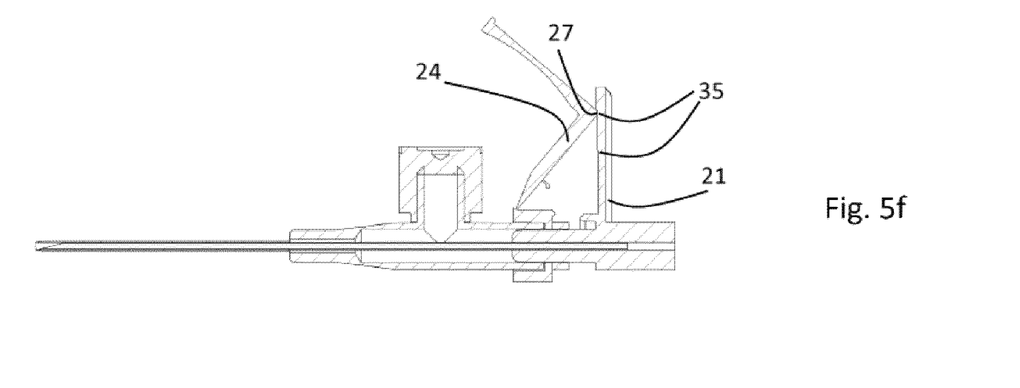

FIG. 5f illustrates an embodiment where the levering arm 24 has an L-like shape, and an outer angle of the L-like shape acts as an interacting member 27. In this embodiment, the grip plate 21 is provided with stop surfaces 35 in the shape of edges that are arranged in an opposite direction compared to the embodiment shown in FIGS. 5a-b.

Figure 6:
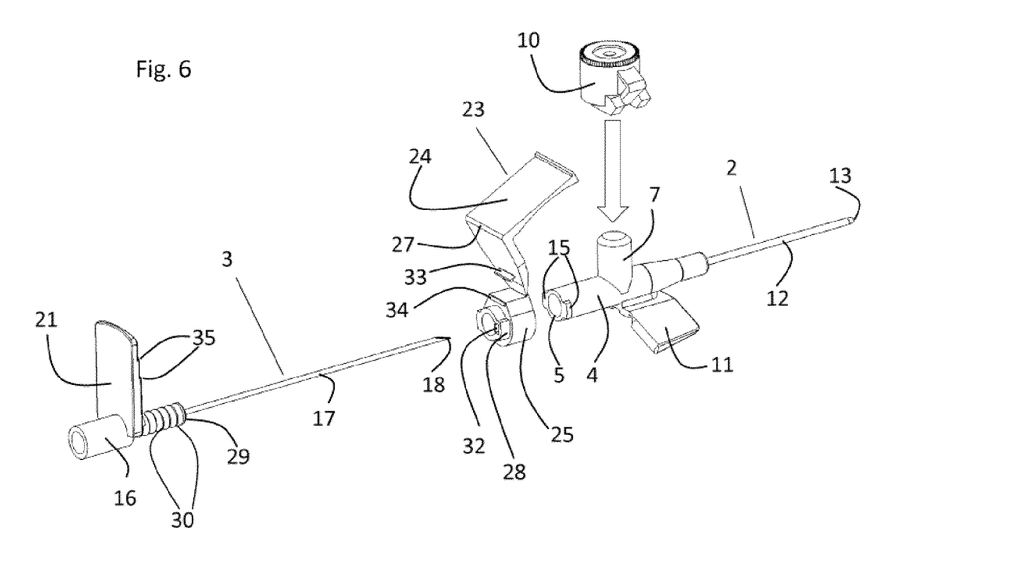
FIG. 6 shows a perspective view of the parts comprised in the catheter device according to an embodiment of the present disclosure.

FIG. 6 illustrates another embodiment of the catheter device 1 according to the present disclosure. Many features are identical to those in FIG. 1a, and the references to those features are the same in FIG. 6. The extended portion 29 of the needle 3 is provided with ribs 30 that circumvent the extended portion 29 radially from the axis A-A (not indicated), and the proximal end the connector 25 of the levering member 23 is provided with a locking flange 32, adapted to engage with the ribs 30 on the extended portion 29 of the needle 3 when the catheter 2 is motioned distally in relation to the needle 3.

Figure 7A:
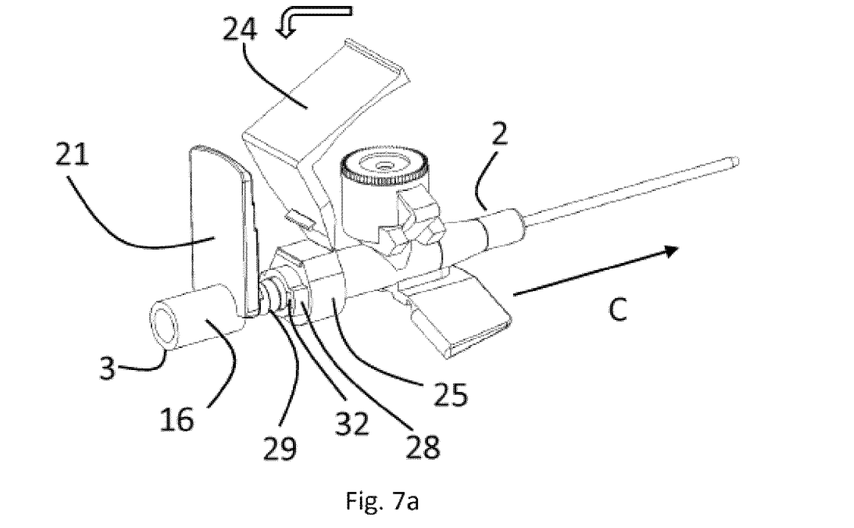
FIGS. 7a and 7b show perspective views of the embodiment of FIG. 6, illustrating the function of the extended portion according to an embodiment of the present disclosure.
Figure 7B:
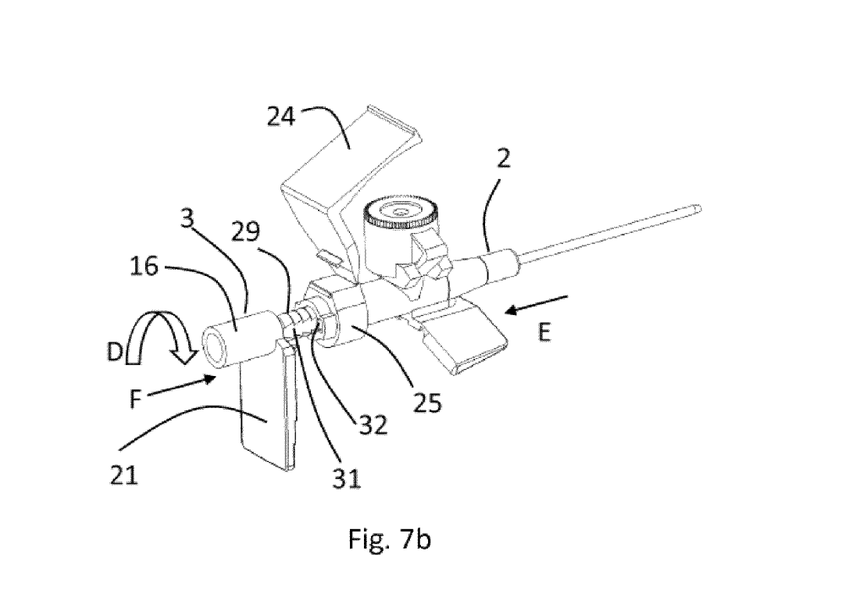

FIGS. 7a and b further illustrates the function of the extended portion 29. The extended portion 29 of the needle 3 comprises a chamfered surface 31 along one side of the entire extended portion 29, leading to a cross-sectional U-shape of the extended portion 29. By lowering the levering arm 24 as indicated by the arrow B in FIG. 7a, the catheter 2 is motioned distally in a direction C in relation to the introducer needle 3. The ribs 30 (not indicated) will engage with the locking flange 32, in order to prevent the needle 3 from being reinserted distally into the catheter 2. By rotating the needle 3 as indicated by the arrow D in FIG. 7b, the chamfered surface 31 is aligned with the locking flange 32, and thereby it is possible to reinsert the needle 3 into the catheter, as indicated by the arrow F, or to reposition the catheter 2 by pulling it proximally as indicated by the arrow E. The exact positioning of the locking flange 32 and the chamfered surface 31 is not of importance, as long as they are not aligned when the grip plate is facing the upper side and aligned with the connecting port on said upper side, i.e. the arrangement of the catheter device needle for insertion of the catheter into a patient.

The person skilled in the art realizes that the present invention is not limited to the preferred embodiments described above. The person skilled in the art further realizes that modifications and variations are possible within the scope of the appended claims. For example, the exact shape of the levering arm, the stop surfaces or interacting members are possible to vary without departing from scope of the appended claims. Additionally, variations to the disclosed embodiments can be understood and effected by the skilled person in practicing the claimed invention, from a study of the drawings, the disclosure, and the appended claims.

The invention claimed is:

1. A catheter device (1) having an axis A-A, a lower side (L) adapted to face a patient, and an upper side (U) opposite the lower side (L) adapted to face away from the patient, said catheter device (1) comprising a catheter (2) and a hypodermic introducer needle (3), the catheter (2) comprising an axially elongated housing (4) having a proximal open end (5) adapted to receive a coupling mechanism or a plug, said elongated housing (4) further comprising an internal passage (6), a connecting port (7) with an internal orifice (8) arranged on the upper side (U) of the catheter device (1), and protrusion members (15) on an outer surface of the proximal open end (5), said catheter (2) further comprising a flexible catheter tube (12) connected to the elongated housing (4), said flexible catheter tube (12) comprising a distal tip end (13) and a lumen (14), said lumen (14) being in fluid communication with the internal passage (6) of the elongated housing (4);

the introducer needle (3) comprising a proximal head (16), a hollow needle (17) having a distal beveled tip (18), and an extended portion (19,29) connecting the hollow needle (17) with the head (16) and adapted to engage with the proximal open end (5) of the catheter (2) when the introducer needle (3) is inserted into the catheter (2), said head (16) comprising an axial channel (20) in fluid communication with an interior of the hollow needle (17), a grip plate (21) arranged on the head (16) and extending in a direction perpendicular to an axial direction, and an engagement member (22) arranged on the grip plate (21) and protruding distally from said grip plate (21), said catheter (2) and said introducer needle (3) being arranged such that when the introducer needle (3) is inserted into the catheter (2), the grip plate (21) is directed towards the upper side (U) of the catheter (2) and aligned with the connection port (7), and wherein the protrusion members (15) on the proximal open end (5) of the catheter (2) are adapted to engage with the engagement member (22) on the grip plate (21) to prevent the introducer needle (3) from rotating around the axis A-A in relation to the catheter (2), the catheter device (1) further comprising a levering member (23) adapted to be removably attached to the catheter (2) and further adapted to motion the catheter (2) from a retracted proximal position to an advanced distal position in the axial direction in relation to the introducer needle (3), wherein, in the retracted proximal position, the beveled tip (18) of the introducer needle (3) protrudes from the distal tip end (13) of the catheter tube (12), and wherein, in the advanced distal position, the beveled tip (18) of the introducer needle (3) is hooded by the catheter tube (12), said catheter device (1) further comprising visual and/or tactile indicators on the grip plate (21) and/or on the extended portion (19, 29) to indicate at least one of a) the catheter (2) being advanced a distance d, said distance d corresponding to a length of the beveled tip (18) of the introducer needle (3), and b) the catheter (2) being advanced a distance D, said distance D corresponding to a distance greater than the length of the beveled tip (18) of the introducer needle (3).

2. The catheter device (1) according to claim 1, wherein the levering member (23) comprises a levering arm (24) and a connector (25) for connecting with the catheter (2).

3. The catheter device (1) according to claim 2, wherein said connector (25) further comprises engagement recesses (26) adapted to engage with the protrusions (15) on the proximal open end (5) of the catheter (2) to removably connect the levering member (23) to the catheter (2).

4. The catheter device (1) according to claim 2, wherein the indicators comprise stop surfaces (35) arranged on the grip plate (21) such that the levering member (23) will engage with said stop surfaces (35), providing a tactile indication for the user.

5. The catheter device (1) according to claim 4, wherein the stop surfaces (35) comprise grooves, protrusions or edges arranged on the grip plate (21).

6. The catheter device (1) according to claim 4, wherein the levering arm (24) comprises an interacting member (27) adapted to interact with the stop surfaces (35) of the grip plate (21).

7. The catheter device (1) according to claim 6, wherein the levering arm (24) has an L-like shape or a curved shape and is arranged on the catheter (2) such that the interacting member (27) comprises an angle of the L-like shape, a convex surface of the curved shape, or a ridge on said convex surface adapted to engage with the stop surfaces (35) of the grip plate (21).

8. The catheter device (1) according to claim 4, further comprising an extended portion (29) of the introducer needle (3) provided with ribs (30) that circumvent the extended portion radially from the axis A-A, and the proximal open end (5) of the catheter (2) or the connector (25) of the levering member (23) is provided with a locking flange (32), adapted to engage with the ribs (30) on the extended portion (29) of the introducer needle (3) when the catheter (2) is motioned distally in relation to the introducer needle (3), the ribs (30) optionally being marked in order to indicate at least one of the positions of the beveled tip (18) of the introducer needle (3) in relation to the distal tip end (13) of the catheter tube (12).

9. The catheter device (1) according to claim 2, wherein the indicators are arranged on the extended portion (19, 29) of the introducer needle (3).

10. The catheter device (1) according to claim 9, wherein the extended portion (29) of the introducer needle (3) is provided with ribs (30) that circumvent the extended portion (29) radially from the axis A-A, and the proximal open end (5) of the catheter (2) or the connector (25) of the levering member (23) is provided with a locking flange (32) adapted to engage with the ribs (30) on the extended portion (29) of the introducer needle (3) when the catheter (2) is motioned distally in relation to the introducer needle (3), the ribs (30) being marked in order to indicate at least one of the positions of the beveled tip (18) of the introducer needle (3) in relation to the distal tip end (13) of the catheter tube (12).

11. The catheter device (1) according to claim 10, wherein the extended portion (29) of the needle comprises a chamfered surface (31) along one side of the entire extended portion (29), leading to a cross-sectional U-shape of the extended portion (29).

12. The catheter device (1) according to claim 10, wherein the indicators comprise markings of the ribs (30) that will correspond to the catheter (2) being advanced a specified distance, providing a visual indication for the user, in addition to a tactile indication provided by each rib (30) being pulled over and engaging with the locking flange (32).

13. The catheter device (1) according to claim 2, wherein the levering arm (24) comprises a lug (33) and the elongated housing (4) of the catheter (2) or a proximal end of the connector (25) of the levering member (23) comprises a retainment element (34), said retainment element (34) being adapted to engage with the lug (33) such that the levering member (23) may reversibly lock the catheter device (1) in a fully advanced position.

14. The catheter device (1) according to claim 1, wherein the levering member (23) interacts with the grip plate (21) of the introducer needle (3) to motion the catheter (2) to advance distally.

15. The catheter device (1) according to claim 1, wherein the levering member (23) is adapted to be removably attached to the connecting port (7) of the catheter (2).

16. The catheter device (1) according to claim 1, wherein a length of the extended portion (19, 29) of the introducer needle (3) is at least equal to, or larger than a total length that the levering member (23) will advance the catheter (2) when fully advanced.

17. A method of placing a catheter (2) in a blood vessel in a patient using a catheter device (1) according to claim 1, the method comprising the steps of:

i. positioning the catheter device (1) against a skin of the patient, in a location where the catheter (2) is to be placed and advancing the catheter device (1) by a distal motion towards a subcutaneous blood vessel, ii. stopping the distal motion when blood appears in the head (16) of the introducer needle (3), indicating that a blood vessel has been entered, iii. motioning the levering member (23) towards the grip plate (21) while keeping the introducer needle (3) still,
iv. pressing the levering member (23) against the grip plate (21), thereby causing the levering member (23) to glide against the grip plate (21) towards the elongated housing (4), further causing the catheter (2) to move distally in relation to the introducer needle (3) that is kept still, until a first indicator is reached, indicating that the beveled tip (18) of the introducer needle (3) is hooded,
v. further motioning the catheter device (1) into the blood vessel,
vi. further motioning the levering member (23), while keeping the introducer needle (3) still, to further distally advance the catheter (2) into the blood vessel, in one or optionally more than one steps,
vii. attaching the catheter (2) against the skin of the patient by attachment members (11) upon full advancement of the catheter (2) in relation to the introducer needle (3) by use of the levering member (23),
viii. removing the introducer needle (3) and optionally the levering member (23) from the catheter device (1), and sealing the proximal open end (5) of the catheter (2) by use of a removable plug or by connection to an infusion device or the like.

* * * * *